United States Patent [19]

Ueno et al.

[11] Patent Number: 4,868,203
[45] Date of Patent: Sep. 19, 1989

[54] BACTERIAL SUBSTANCE AND PHARMACEUTICAL COMPOSITION THEREOF

[75] Inventors: Ryuzo Ueno, Nishinomiya; Ryuji Ueno, Kyoto; Hiroshi Kita, Takarazuka; Ichie Kato, Kawanishi; Akihiko Tabata; Takashi Hironaka, both of Nishinomiya, all of Japan

[73] Assignee: Kabushikikaisha Ueno Seiyaku Oyo Kenkyujo, Hyogo, Japan

[21] Appl. No.: 53,021

[22] Filed: May 22, 1987

[30] Foreign Application Priority Data

Jun. 2, 1986 [JP] Japan .................................. 61-128846
Feb. 27, 1987 [JP] Japan .................................. 62-46317

[51] Int. Cl.⁴ .................. C07D 207/333; A61K 31/40
[52] U.S. Cl. ..................................... 514/423; 548/540
[58] Field of Search ............... 548/530, 540; 514/424, 514/423

[56] References Cited

U.S. PATENT DOCUMENTS 4,683,230  7/1987  Tsuhakawa et al. ................ 548/530

OTHER PUBLICATIONS

Maresz–Babczyszyn, J., et al. *Arch. Immun. et Therapiae Experimentalis* 18:501–506 (1970).
Nakanishi, T. et al., *Chem. Pharm. Bull.* 24:2955–2960 (1976).

*Primary Examiner*—David B. Springer
*Attorney, Agent, or Firm*—Saidman, Sterne, Kessler & Goldstein

[57] ABSTRACT

A bacterial substance UFC-N11 of the formula:

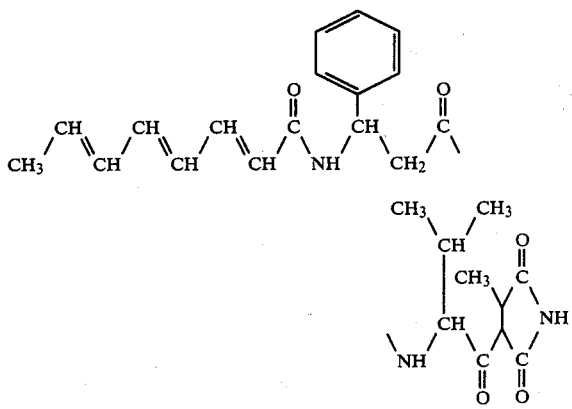

2 Claims, 5 Drawing Sheets

BACTERIAL SUBSTANCE AND PHARMACEUTICAL COMPOSITION THEREOF

BACKGROUND OF THE INVENTION

Field of the Invention

The present invention relates to a novel bacterial substance which have been designated UFC-N11, a process for production thereof and use of the said substance in pharmaceutical, agricultural, preservative and piscicultural compositions.

Although there have been a great number of substances known to have antibacterial activities, most of them are of less practical use or otherwise involve problems such as occurence of resistant bacteria. Therefore, there is a continuous need for novel antibacterial substances. The present inventors have studied on various products of a great variety of bacteria separated from natural sources and have found the fact that a certain species of bacteria belonging to the genus Enterobacter produces antibacterially active substance. Further, the present inventors successfully separated the said substance in the form of crystals and confirmed that it is a novel substance having antibacterial activity which allows its use ina pharmaceutical composition for treatment of bacterial infection in humans or animals, in a agricultural composition for treatment of diseases of farm or garden plants, in a preservative useful for improvement of preservability of food, in a piscicultural composition for treatment of diseases of fishes and as a synthetic intermediate. The present invention has been completed based upon such recognition.

SUMMARY OF THE INVENTION

In the first aspect, the present invention provides a bacterial substance UFC-N11 of the formula:

[chemical structure]

In the second aspect, the present invention provides a process for producing the said bacterial substance UFC-N11 which comprises culturing microorganism belonging to the genus Enterbacter and capable of producing the said substance UFC-N11 in contact with the nutrient medium and recovering the produced substance UFC-N11 from the culture.

In the third aspect, the present invention provides a pharmaceutical composition comprising bacteriocidally effective amount of the said bacterial substance UFC-N11 in association with a pharmaceutically acceptable carrier, diluent or excipient.

In the fourth aspect, the present invention provides a agricultural composition comprising bacteriocidally effective amount of the said bacterial substance UFC-N11 in association with a agricultural acceptable carrier, diluent or excipient.

In the fifth aspect, the present invention provides a preservative composition for foods comprising bacteriocidally effective amount of the said bacterial substance UFC-N11 in association with a sitologically acceptable carrier, diluent or excipient.

In the sixth aspect, the present invention provides a pisicultural composition comprising bacteriocidally effective amount of the said bacterial substance UFC-N11 in association with a pisicultural acceptable carrier, diluent or excipient.

In the seventh aspect, the present invention provides a microorganism belonging to the genus Enterobacter and capable of producing the said bacterial substance UFC-N11.

In the eighth aspect, the present invention provides a method of treating human or animal or plant diseases which comprises administering bacteriocidally effective amount of the bacterial substance UFC-N11 to a subject in need of such treatment.

In the ninth aspect, the present invention provides a use of the said bacterial substance UFC-N11 for the manufacture of medicament for treating human, animal plant or fish diseases caused by bacteria.

DETAILED DESCRIPTION AND PREFERRED EMBODIMENT

The term "treatment" used herein is intended to cover all the controls of diseases including prevention, sustention (i.e. prevention of aggravation), alleviation and therapy.

The said bacterial substance UFC-N11 has the following characteristics:

(a) Elemental analysis (%): C=67.60, H=6.89, N=8.75 and O=16.76.

Figure 1:
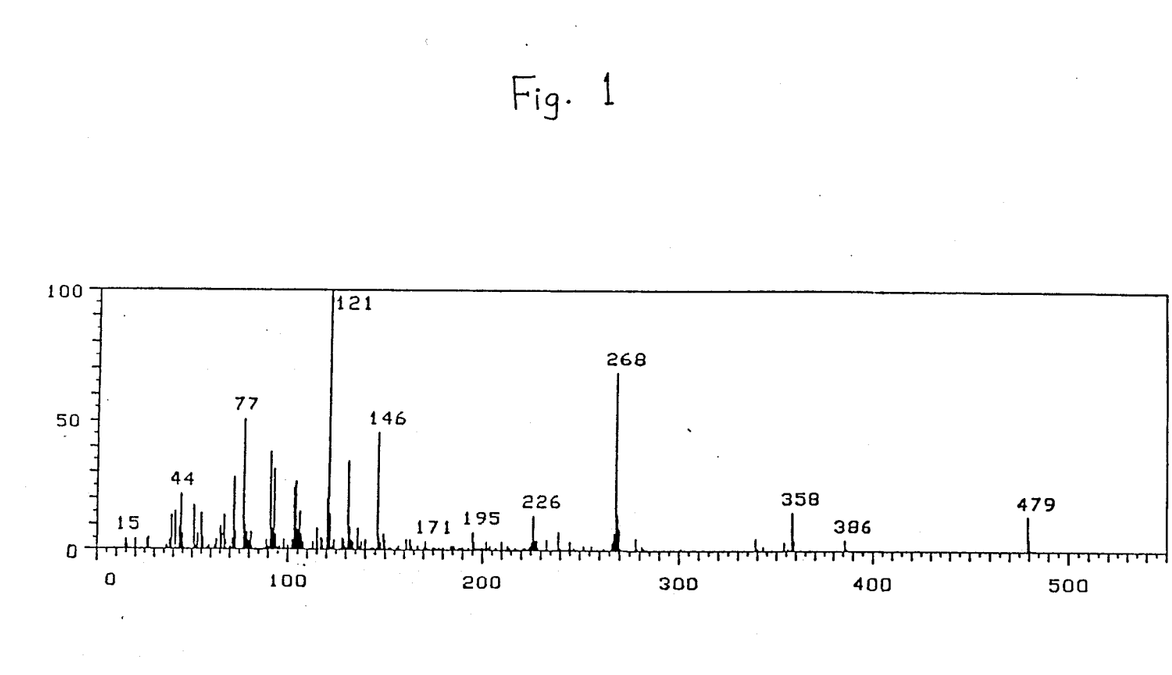

(b) Molecular weight=479 (mass spectrometry, see FIG. 1)

(c) Melting point=146° C.

Figure 2:
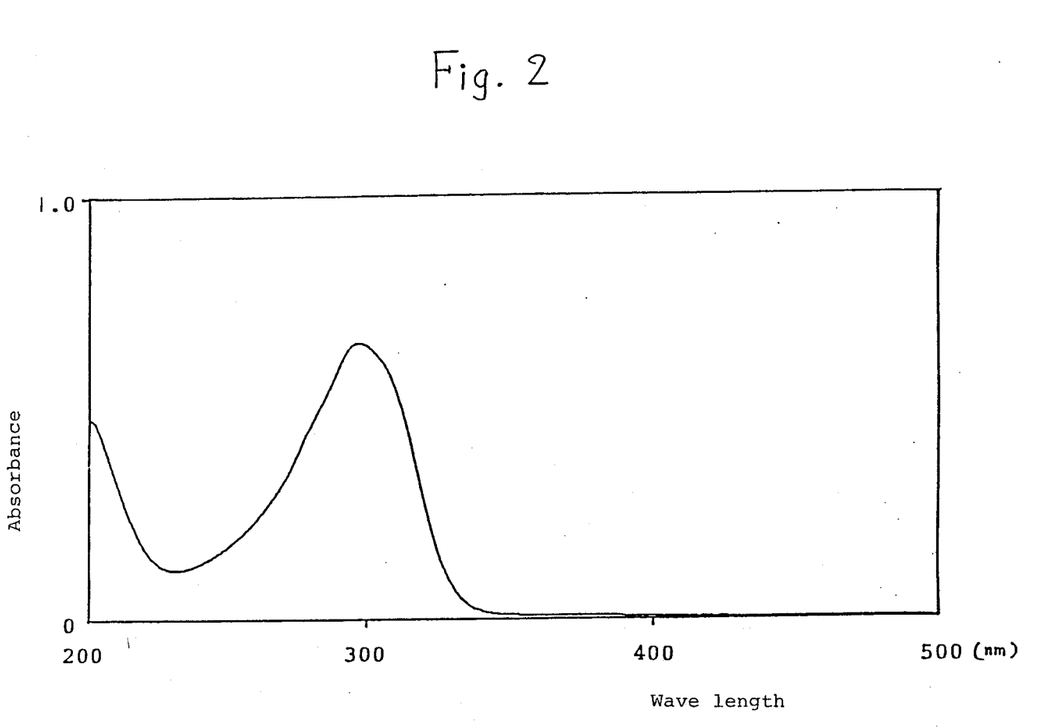
Figure 3:
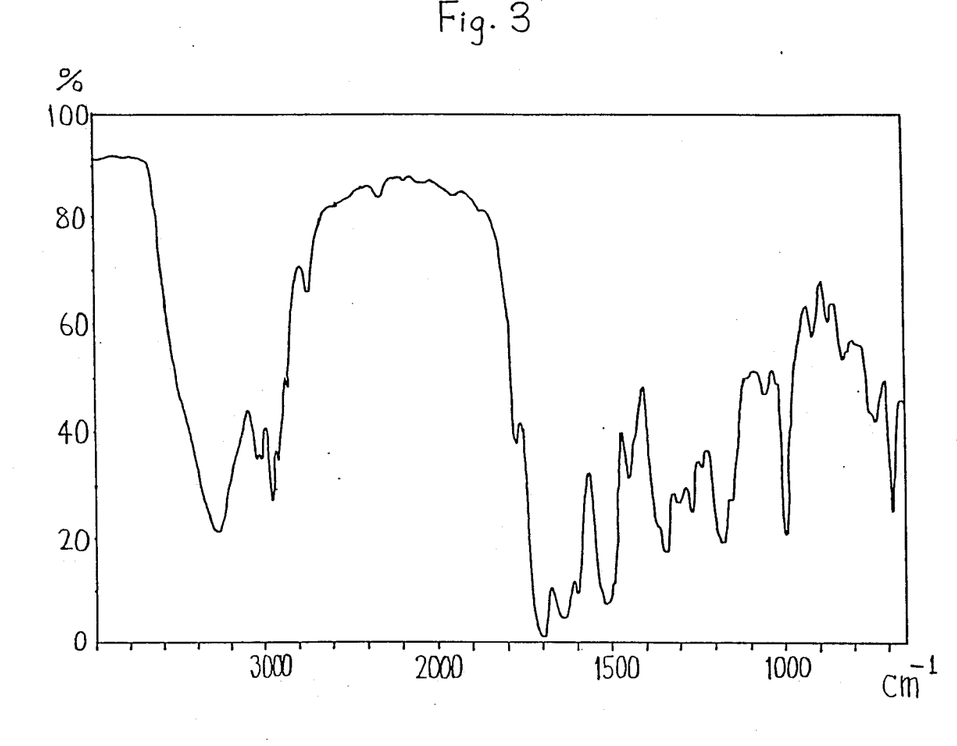

(d) UV spectrum (methanol, see FIG. 2):$\lambda_{max}$=297 nm (e) IR spectrum (KBr, see FIG. 3): ca. 3260, 3035, 3005, 2945, 2910, 2855, 2740, 2310, 1770, 1700, 1640, 1595, 1510, 1440, 1340, 1300, 1260, 1230, 1175, 1050, 990, 915, 870, 830, 730 and 680 cm$^{-1}$.

Figure 4:
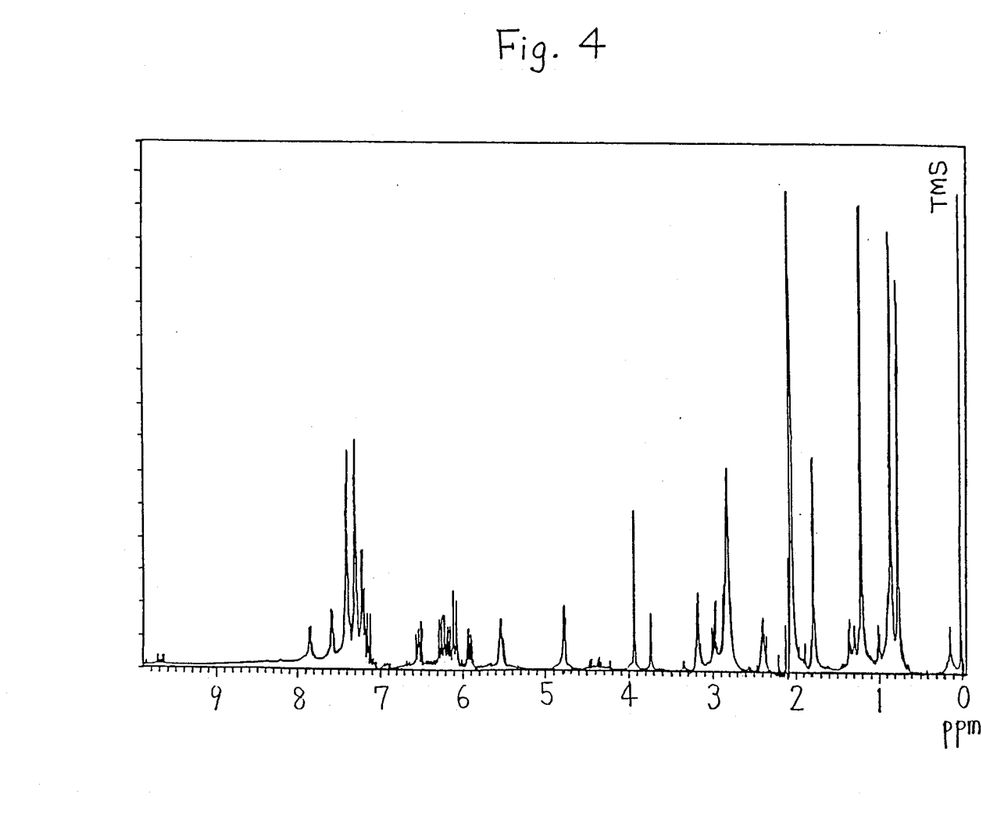

(f) $^1$H-NMR spectrum (acetone-d6, see FIG. 4):$\delta$=0.77, 0.86, 1.21, 1.78, 2.38, 2.81, 3.17, 3.93, 4.77, 5.52, 5.92, 6.24, 6.56, 7.39, 7.57 and 7.86

Figure 5:
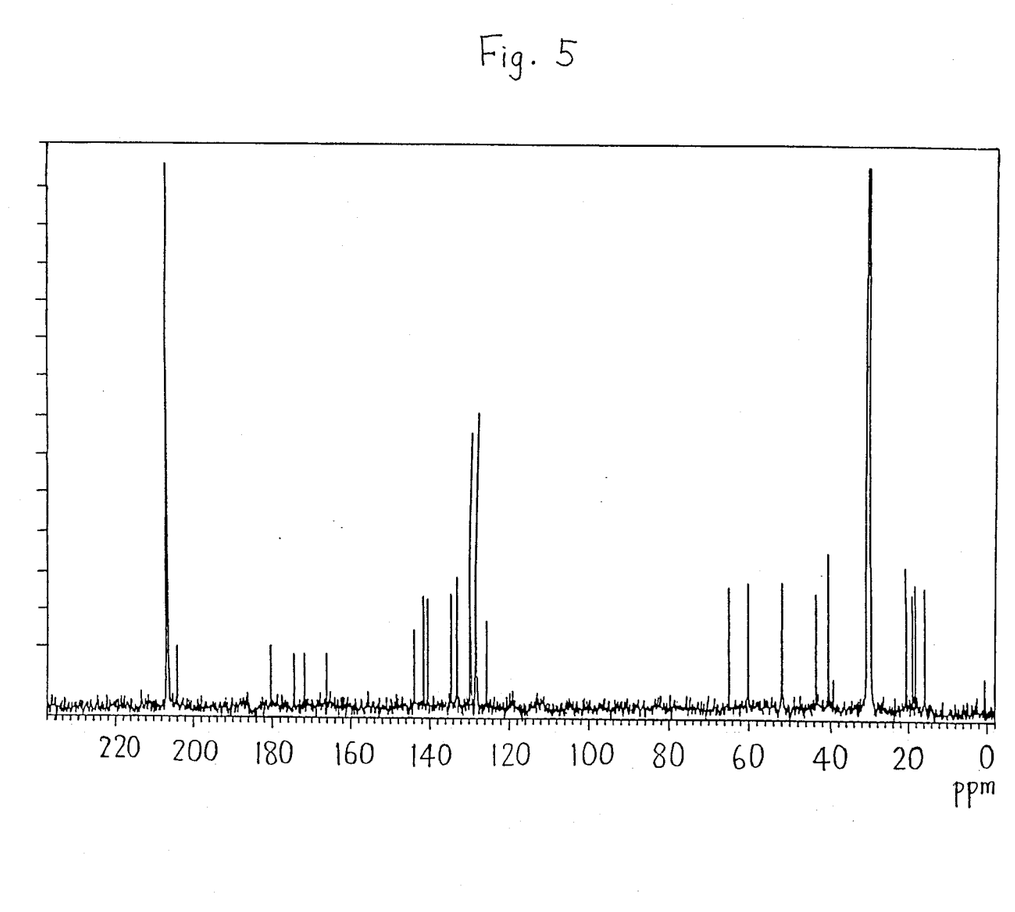

(g) $^1$H-NMR spectrum (acetone-d6, see FIG. 5)$\delta$=15.10 17.55, 19.97, 20.18, 39.83, 39.92, 42.99, 51.39, 59.59, 64.37, 124.97, 127.38, 127.74, 127.86, 129.09, 129.20, 129.36, 132.43, 133.96, 139.98, 141.06, 143.88, 165.64, 171.30, 173.97, 179.79 and 203.49

(h) Solubility in various solvents: soluble in pyridine, acetic acid, dimethyl sulfoxide, methanol, ethanol, acetone, ethyl acetate and dimethyl ether. slightly soluble or insolbule in n-hexane, chloroform, benzene and water.

(i) Color reaction: positive to sulfuric acid and iodine.

(j) Thin layer chromatography: $R_f$=0.51 (developing solvent: dichloromethane/ethyl acetate=1/2)(silica gel 60 produced by Merk. & Co., Inc.) $R_f$=0.42 (developing solvent: 70% methanol)(RP18, produced by Merk & Co., Inc.)

(k) Color: white to pale pink

The above bacterial substance UFC-N11 can be obtained by culturing bacteria which belong to the genus Enterobacter and which are capable of producing the substance UFC-N11 on a nutrient medium. Among such bacteria, especially suitable one for the production of bacterial substance UFC-N11 is a strain, tentatively designateted N11, separated from natural source in Sandashi, Hyogo-ken, Japan. This strain has the microbiological properties as follows:

| Properties and cultural observation on various differential media: | |
| --- | --- |
| Gram's stain | negative |
| Shape | rods |
| Size | 0.2 × 1–1.5 μm |
| Sporulation ability | nil |
| Mobility | some |
| Flagellum | peritrichous flagella |
| Acid-fast stain | nil |
| Bouillon agar plate medium | good growth |
| MacConkey's plate medium | good growth |
| PEA plate medium | no growth, |
| Columbia CNA plate medium | no growth |
| Colony on bouillon agar plate medium | diameter = 1.5 mm. S-type. milky yellow, semitransparent at 30° C. for 18 hours diameter = 4 mm, S-type, milky yellow. semitransparent at 30° C. for 48 hours. |
| Colony on bouillon agar slant medium | almost same as those formed on bouillon agar plate medium |
| Growth on meat infusion broth | generally uniform growth. slightly better at upper portion. sometimes thin pellicle is formed |
| Litmus milk | litmus slightly changed to red. milk coagulated upon ca. 8-day culture |
| Pigment production (King A) | water-insoluble lemon yellow pigment is produced |
| Pigment production (King B) | water-insoluble lemon yellow pigment is produced |
| Oxygen requirement | nil (growable under both anaerobic and aerobic conditions) |
| Growable pH | 4–9 |
| Optimal pH | 5–8 |
| Growable temperature | growable at 37° C., not growth at 40° C. |
| Optimal temperature | 25–37° C. |
| NaCl requirement | nil (growable without NaCl or with 6% NaCl) |
| NaCl 0% | +++ |
| 3% | ++ |
| 6% | + |
| Gelatin liquefaction | +w (at 30° C. for 8 days) |
| Chitin decomposition | − (at 30° C. for 14 days) |
| Cytochrome oxidase | − |
| Catalase | + |
| OF test | F |
| Amino acid decomposition | |
| Arginine | − |
| Lysine | − |
| Ornithine | − |
| Indole | + |
| MR | − |
| VP | + |
| Citrate utilization (Kozel) | + |
| Citrate utilization (Christensene) | + |
| Nitrate reduction | − |
| IPA | − |
| $H_2S$ | − |
| Denitrification | − |
| Starch hydrolysis | − |

| Utilization of sugar and production of gases | Utilization of sugar | Production of gases |
| --- | --- | --- |
| D-Glucose | + | − |
| L-Arabinose | + | − |
| D-Xylose | + | − |
| D-Mannose | + | − |
| D-Fructose | + | − |
| D-Galactose | + | − |
| Maltose | + | − |
| Sucrose | + | − |
| Lactose | + | − |
| Trehalose | + | − |
| D-Sorbitol | + | − |
| D-Mannitol | + | − |
| Inositol | + | − |
| Glycerol | + | − |
| Starch | + | − |
| Adonitol | − | − |
| Rhamnose | − | − |

On the basis of the aforementioned characteristics, it considered is reasonable to classify the strain N-11 as a species of the genus Enterobacter. Within this genus most related species is Enterobacter agglomeraus according to the characteristics. However, in view of the fact that the strain N-11 is some what different in characteristics from the above species and that it has an important characteristics of producing novel substance UFC-N11 was identified as a novel strain Enterobacter sp. N11.

Any species corresponding to the strain N11 is not described in Bergey's Manual of Systematic Bacteriology. Vol. 1 and Identification of Medical Bacteria. Ed. 2.

The above strain N11 has been deposited under Budapest Treaty with Fermentation Research Institute (Japan) with the accession No. FERM BP-1337.

According to the present invention, the bacterial substance UFC-N11 may be produced by cultivating a microorganism capable of producing the said substance in a nutrient medium. In principle, the cultivation may be carried out according to the general method for cultivation of microorganism but generally it is advantageous to carry out the cultivation by submerged liquid culture. Any medium containing nutrients which can be utilized by UFC-N11 producing bacterial such as synthetic, semisynthetic and natural media can be used. In the composition of the medium. Glucose, starch, glycerol and the like may. be used as a carbon source and meat extract, peptone, gluten meal, soybean flour, corn steep liquor, dry yeast, ammonium sulfate, urea and the like may be used as a nitrogen source. Further, metal salt such as calcium carbonate, phosphate or the like may be optionally added. When excessive foaming occurs during cultivation, it is preferable to add a suitable defoaming agent such as silicone, vegetable oil or the like. The incubation temperature may be similar to that for the conventional mesophilic bacteria but preferably is around 30° C. When cultivation is in large scale, seed culture may be optionally carried out. The incubation period for the culture is about 15–50 hours.

The bacterial substance UFC-N11 accumulated in the culture are usually contained in the bacterial cells or the culture medium and can be recovered from the cells or the medium after separating bacterial cells by centrifugation or filtration. Suitable separating means may utilize differences in solubility in an appropriate solvent, in deposition rate from the solution, in affinity to absorbent, in partition ratio between two liquid phases and the like and they may be applied in combination in optional order or repetition.

Since the bacterial substance of the present invention UFC-N11 has remarkable antibacterial activity against pathogenic bacteria etiegenic to human or animal diseases such as Staphylococcus, Bacillus, Salmonella, it is useful in preparing medicament for treatment of bacterial infection to human or animals. For this purpose, the dosage may vary depending on the mode of application, kind of disease, age and particular condition of subject, and the like but is sufficient to exhibit anitbacterial activity in the body. Generally, the dosage in the range from about 0.1 to 200 mg/kg, preferably from about 1 to 50 mg/kg, may bring about a satisfactory result. For human subjects, the daily dosage is usually in the range from about 20 mg to 20 g, preferably from about 100 mg to 10 g, administered in 1 to 4 divided doses a day in unit dosage form or in sustained release form. Any application route such as oral, local or injective administration may be employed.

For administration, the active ingredient may be mixed with pharmaceutical carrier such as organic or inorganic, solid or liquid excipient which is suitable for the selected mode of application such as oral application or injection, and administered in the form of a conventional pharmaceutical preparation. Such preparation includes solid such as tablets, granules, powders, capsules, and liquid such as solution, emulsion, suspension and the like. Said carrier includes starch, lactose, glucose, sucrose, dextrine, cellulose, paraffin, fatty acid glyceride, water, alcohol, gum arabic and the like. If necessary, auxiliary, stabilizer, emulsifier, lubricant, binder, pH adjustor controller, isotonic agent and other conventional additives may be added.

Also, the bacterial substance UFC-N11 has remarkable antibacterial activity against Pseudomonas, Xanthomonas, Cornebacterium, Erwinia and the like which are pathogenic to plants. Since all the known plantpathogenic bacteria fall under these four gena, the present bacterial substance UFC-N11 is useful as pesticide for treatment of plant diseases such as bacterial wilt, black rot bacterial shot-hole, soft rot, bacterial spot, bacterial canker, bacterial leaf blight and the like of vegetables, fruit trees, rice plant, wheat and the like. For this purpose, the application rate may vary depending on the mode of application, kinds of diseases, condition of plants and the like, but it is generally from about 0.5 to 100 ppm, preferably about 1 to 50 ppm) when applied to plants), or from about 1 to 500 g/a, preferably about 2 to 200 g/a (when applied to soil).

For the application, the active ingredients may be mixed with pesticidal carrier such as organic or inorganic, solid or liquid vehicle which is suitable for particular mode of application such as spraying on leaves, dipping, spreading onto the soil and the like, and applied in the form of conventional pesticidal preparation. Such preparation includes powders, glanules, tablet, wettable powder, solution oil, emulsifiable concentrate, suspension, flowable, fumigant, aerosol and the like. The suitable carrier includes water, ethanol, ethylene glycol, dimethylformamide, dimethyl sulfoxide, acetone, petroleum benzine, talc, clay, kaolin, diatomaceous earth, calcium carbonate, starch and the like. Also, adjuvant such as spreader, emulsifier, surfactant, dispersant, wetting agent, stabilizer and other fungicide, herbicide, germicide, plant growth regulator, fertilizer and the like may be mixed or used in combination.

Further, since the bacterial substance UFC-N11 has antibacterial activity as described above, it is useful as a preservative for meat product, fish product, vegetable product, tofu, confectionery, fruit juice, potable water and the like. For this purpose, the amount to be used varies depending on the kind of food particular object and the like, but it will be generally about 0.05 to 100 ppm, preferably about 0.1 to 50 ppm.

Still further, the bacterial substance UFC-N11 has pronounced anti-bacterial activity against the bacteria which are pathogens of the diseases of fishes such as, for example, Aeromonas, Vibrio, Edwardsiella, Flexibacter, Pasteurella, etc. and is therefore useful as a piscicultural pesticide for prevention or therapy of scale disease of Cyprinids, furunculosis of salmonids such as salmon, trout, etc., Vibrio disease of sweetfish, young yellowtail, etc., Edwardsiellosis of eel, etc., colummaris disease of eel, carp, etc., pseudotuberculosis of yellowtail, horse mackerel, etc.

The dosage for this purpose may be such amount as to allow absorption in the living fish at a concentration higher than the minimum growth inhibiting concentration, which, of course, will vary depending on administration mode, kind of disease, etc. A satisfactory result will generally be obtained at a dose of about 10 to 100 mg/kg body weight of fish.

As to the administration method, UFC-N11 may be orally administered (or allowed to take) together with a feed, or it may be dissolved in water in a suitable dosage form whereby the fishes may be subjected to drug bathing therein. That is to say, any formulation or administration form may be adopted in so far as the active ingredient may be absorbed into the fish body.

In the oral administration method, the substance UFC-N11 may be administered, for example, by a method wherein the substance is mixed in the form of powders into a mince of raw feed (such as sardine, sand eel, mackerel, etc.), assorted feed, or a feed made by mixing a mince of raw feed with an assorted feed, by a method wherein the substance in the form of spreading composition is attached to the surface of a chopped raw feed, or a method the substance in the form of an aqueous solution is permeated into the solid assorted feed.

The method of subjecting the fish to drug bathing includes, for example, a method of wherein the fishes are bathed in a hatch during transportation; a method of wherein fishes are bathed by use of a large water tank (for example, a 1-ton water tank) on transferring the fish from a ship to a fish preserve; a method wherein fishes are bathed in a covered fish preserve supplying oxygen with a blower; or, in case of the fresh water fishes, a method wherein fishes are bathed in the breeding pool per se while the supplying water to the breeding pool is stopped.

As the vehicles for the drug composition, there may be used saccarides, carbohydrates, fats and fatty oils, solvents, surfactants, water, etc. which are harmless to the fish.

The substance of the present invention can also be used as a synthetic starting material for production of other antibacterially or otherwise active substance.

The present invention will be further illustrated in detail in the following examples and test examples.

EXAMPLE 1

Production of bacterial substance UFC-N11

A medium (7.5 ml) containing bacto-triptone (15 g/l), bacto-soytone (3g/l), NaCl (5 g/l), bacto-dextrose (2.5 g/l) and potassium phosphate (2.5 g/l (hereinafter referred to as Medium A) was dispensed in test tubes, sterilized, inoculated wit one loopful of Enterobacter sp. N11 obtained from a slant culture and incubated statically at 28° C. for 24 hours.

Then, Medium A (150 ml) was dispensed in a shaking flask (500 ml), sterilized, inoculatd with above seed bacteria (7.5 ml) and cultured at 28° C. for 24 hours on a reciprocal shaker. Subsequently. Medium A (7 lit) was poured, in a culture jar sterilized, inoculated with above seed bacteria (350 ml) and incubated at 30° C. for 24 hours with agitation and aeration (0.25 v/v/min., 400 rpm, pH 7.0).

The culture was centrifuged at 8000 rpm for 20 minutes and the supernatant was separated from the bacterial cells. Diaion HP-20 (nonionic resin manactured by Mitsubishi Chemical Industries Limited)(1.4) was added to the supernatant and stirred at room temperature for 24 hours. The above Diaion resin was packed in a column and sequentially washed with water (5 liter) 30% aqueous methanol and 60% aqueous methanol, and then eluted with methanol. The eluate was concentrated under reduced pressure, combined with water (pH=3) and extracted with three portions of ethyl acetate. The combined extracts were washed with water and concentrated under reduced pressure. The residue was applied on silica gel column (silica gel 60 No. 7734 manufactured by Merk & Co., Inc.), developed and eluted with a mixed solvent of dichloromethane : ethyl acetate (1:2). The eluate was concentrated under reduced pressure and subjected to HPLC [YMC-pack A-343 (S-5. ODS manufactured by Yamamura Kagaku Kenkyusho), 20×250 mm, 70%–100 % aqueous methanol gradient] to give the bacterial substance UFC-N11 (300 mg). The bacterial cells were extracted with acetone and the extract was treated in a similar manner by carrying out concentration, extraction with ethyl acetate, chromatography over silica gel column and HPLC to give the bacteria substance UFC-N11 (500 mg).

| Formulation 1: Tablets | |
|---|---|
| Bacterial substance UFC-N11 | 200 mg |
| Corn starch | 45 mg |
| Lactose | 300 mg |
| Magnesium stearate | 5 mg |

The above components were mixed, granulated and pressed to produce tablets by the conventional process.

| Formulation 2: Wettable powder | |
|---|---|
| Bacterial substance UFC-N11 | 20 parts |
| Clay | 68 parts |
| Sodium ligninsulfonate | 4 parts |
| Sodium alkylbenzenesulfonate | 8 parts |

Above components were mixed and ground to produce wettable powder.

| Formulation 3: Emulsifiable concentrate | |
|---|---|
| Bacterial substance UFC-N11 | 10 parts |
| Xylene | 30 parts |
| Dioxane | 40 parts |
| Oxyethylenealkylaryl ether | 20 parts |

Above components were mixed to produce emulsifiable concentrate.

TEST EXAMPLE 1

Minimum growth inhibitory concentration

The minimum growth inhibitory concentration (MIC) values of bacterial substance UFC-N11 to various kinds of bacteria determined according to the conventional method were measured in the conventional manner. The results are as follows:

| | MIC ($\mu$g/ml) |
|---|---|
| *Staphylococcus aureus* 209-P | 1.56 |
| *Pseudomonas aeruginosa* | 50 |
| *Salmonella typhimurium* | 6.25 |
| *Klebsiella pneumoniae* | 12.5 |
| *Campylobacter fetus* | 1.56 |
| *Campylobacter jejuni* | 0.78 |
| *Bacillus subtilis* 6633 | 0.39 |
| *Escherichia coli* NIHJ JC-2 | 1.56 |
| *Salmonella enteritidis* 1891 | 0.78 |
| *Enterobacter cloacae* IID977 | 25 |
| *Proteus vulgaris* OX-19 | 0.195 |
| *Pseudomonas syringae* PV Mori NIAES 1020 (bacterial rugose) | 25 |
| *Pseudomonas syringae* PV *lachrymans* NIAES 1316 (angular leaf spot of cucumber) | 6.25 |
| *Pseudomonas syringae* PV *tabaci* NIAES 1075 | 12.5 |
| *Pseudomonas solanacearum* NIAES 1418 (wilt of solanum) | 1.56 |
| *Xandomonas campestris* PV *citri* U-2 (citrus canker) | 0.2 |
| *Xandomonas campestris* FV Pruni 7855SMR (bacterial spot of peach) | 0.1 |
| *Xandomonas campestris* PV *campestris* NIAES 1152 (black rot) | 0.1 |
| *Xandomonas campestris* PV *oryzae* H75373 | 0.05 |
| *Corynebacterium michiganence* PV *michiganene* NIAES 1044 (bacterial canker of tomatoes) | 6.25 |
| *Ervinia carotovara* subsp. *carotovora* NIAES 1393 (black leg of potatoes) | 6.25 |

TEST EXAMPLE 2

Evaluation of activity against the canker of citrus

Triennial potted seedlings of nable (Shiraki) were examined. Xanthomonas campestris PV citri (pathogene of citrus canker) was cultured on potato semisynthetic medium at 27° C. for 24 hours, then suspended in 0.1% aqueous peptone, adjusted to about $10^8$/ml and inoculated on leaves of the seedlings by using 10-needle inoculation process. After 24 hours, bacterial substance UFC-N11 dissolved in 0.05% aqueous sodium bicarbonate was sprayed in the form of 20 ppm or 40 ppm solution. A solution without the substance N11 was used as the control. Subsequently, the seedlings were grown in a plastic greenhouse. After 14 days, number of affected spores was counted and prevention ratio was calculated from percentage of affected spores according to the following formula:

$$\text{Prevention}(\%) = 1 - \frac{\text{Affected spore of test group}}{\text{Affected spore of control group}} \times 100$$

Results are as follows:

|  | Concentration (ppm) | Prevention (%) | Damage |
|---|---|---|---|
| Test group | 40 | 33.9 | nil |
| " | 20 | 26.70 | nil |
| Control | 0 | 0 | nil |
| Streptomycin | 0 | 30.3 | nil |

TEST EXAMPLE 3

Evaluation of activity against the bacterial spot of cucumber

Cucumber(Green tokiwa) was used for the test. Potted cucumber plants (2 leaf stage) were sprayed with sufficient amount of 50 ppm solution of bacterial substance UFC-N11 (dissolved in 0.05% aqueous sodium bicarbonate), air-dried, and spray-inoculated $10^8$/ml suspension of Pseudomonas Syringae PV lachrymans NIAES 1316, cultured on Wakimoto medium for 3 days, on both sides of leaves. For the control, an experiment was carried out using a solution without the substance N11 in the same manner as described above. After inoculation, the plants were maintained at 28° C. for 24 hours and maintained in a glass house until the day of evaluation. Six days after inoculation, percentage of spots area affected on the first and second seed leaf was observed and protection value was calculated according to the following formula:

$$\text{Protection}(\%) = 1 - \frac{\text{Affected area of test group}}{\text{Affected area of control group}} \times 100$$

The experiment was repeated using $Cu(OH)_2$ (Kosaid) 83% wettable powder (produced by Hokko chemical Industry Co. Ltd.) as a positive reference. In this case $CaCO_3$ (Kurefunon) (produced by Shiraishi Calcium) was added ($\times 200$) in order to reduce damage. Results are as follows:

|  | Concentration (ppm) | Protection | Damage |
|---|---|---|---|
| Test group | 50 | 36.8 | Nil |
| Control | 0 | 0 | Nil |
| 83% wettable powder | 830 | 35.1 |  |

TEST EXAMPLE 4

Kamaboko

Fish paste was prepared by adding NaCl (2.5%), chemical seasoning (0.8%), starch (5%) and ice water (10%) based on frozen surimi of walleye pollack (4 kg) and cutting by a silent cutter for 10 minutes. Predetermined amount of bacterial substance UFC-N11 based on the resulting fish paste (2 kg) was added and completely mixed in a small mixer for 5 minutes. About 100 g fish paste were enclosed with polyvinylidene chloride film (spread width:45 mm), boiled at 90° C. for 30 minutes, quenched, left overnight and then tested for rotproof property.

The test was conducted as follows. As the complete package products, 10 pieces/group of kamaboko processed by casing method samples and, as the simplified package products, 10 pieces/group prepared by peeling off the casing under sterilized condition, cutting into 2 round slices (thickness: 10 mm) by a sterilized knife and placing in a sterilized plastic Petri dish. were placed in a thermostatic chamber at 30° C. and evaluated by macroscopically observation. The evaluation uses five-level scale shown below. The period until the average evaluation value of 1 is attained is defined as the storage life.

| Stage of rotting | Degeneration evaluation | Standard for evaluation |
|---|---|---|
| Without rotting | −0 | Completely preserved (no change). |
|  | ±0.5 | Extremely small spots observed. |
| First stage | +1 | One colony-like spot or partial expansion observed. slightly cloudy liquor separated. |
| Second stage | ++2 | Two or more colony-like spots, or expanded portions observed. cloudy liquor separated. |
| Third stage | +++3 | Many colony-like spots or small expanded portions observed. |
| Fourth stage | ++++4 | Partially expanded or partially softened. |
| Fifth stage | +++++5 | Generally softened and expanded. |

Obtained storage life is shown below:

|  |  |  |  | Storage life (day) | |
|---|---|---|---|---|---|
|  |  | Concentration | pH | simplified package | Complete package |
| Test group | 1 | 0.01 ppm | 7.06 | 2.5 | 5.0 |
|  | 2 | 0.1 ppm | 7.06 | 3.0 | 7.0 |
|  | 3 | 1.0 ppm | 7.05 | 4.5 | 9.0 |
|  | 4 | 10 ppm | 7.05 | 7.5 | 14.0 |
|  | 5 | 50 ppm | 7.04 | 9.0 | 18.0 |
|  | 6 | 100 ppm | 7.06 | 12.0 | 24.0 |
| Without addition |  | 0 | 7.05 | 1.5 | 2.0 |
| Sorbic acid |  | 0.2% | 6.58 | 7.0 | 12.0 |

TEST EXAMPLE 5

Steamed Chinese noodles

Predetermined amount of bacterial substance UFC-N11, NaCl (20 g), powdered Kansui (6 g) and edible Yellow pigment (0.4 g) per 1 kg of flour were dissolved in water (144 ml) and used for watering. After kneading for 10 minutes. the product was rolled and cut with cutting edge (#10) to give noodles. The resulting noodles were steamed at the temperature higher than 98° C. for 6 minutes, washed with water, packed in polyethylene packages (each weighing 40 g) and heated at 85° C. for 30 minutes. The obtained packages containing Chinese noodles (10 bags/group) were maintained at 30° C. and the change in appearance with time was observed and preservation effect was evaluated according to the following evaluation scale. The values shown in the following Table are averaged evaluation levels of degeneration. The period until the average level of 1 is attained is defined as the storage life. As is obvious from the Table, the preservability of the heated and steamed Chinese noodles can be remarkably improved upon addition of bacterial substance UFC-N11.

| Evaluation for degeneration | Standard for evaluation |
|---|---|
| 0 | Completely preserved, no change observed |
| 1 | Color changed, softened, slime, a spot |

-continued

| | | of mold observed |
|---|---|---|
| | 2 | Color changed, softened, two spots of mold observed or area of degeneration extended |
| | 3 | Color changed, softened, slime, mold covered half of the sample |
| | 4 | Color changed, softened, slime, mold covered ¾ of the sample |
| | 5 | Color changed, softened, slime mold grew all over |

| | | Concentration (ppm) | pH of product | Storage life (days) |
|---|---|---|---|---|
| Test | 1 | 0.1 | 9.39 | 6.0 |
| group | 2 | 1.0 | 9.41 | 8.1 |
| | 3 | 10 | 9.40 | 10.0 |
| | 4 | 50 | 9.38 | 16.0 |
| | 5 | 100 | 9.41 | 20.0 |
| No addition | | 0 | 9.40 | 3.8 |

TEST EXAMPLE 6

Potato salad

Bacterial substance UFC-N11 was added to potato (300 g), carrot (50 g), sliced onion (60 g), sliced cucumber (80 g), salad oil (15 g), vinegar (12. 5 g), NaCl (2 g), pepper (0.05 g) and mayonnaise (100 g) (total: ca 620 g) to prepare potato salad. Test samples (20 g/group) were packed in 200 ml mayonnaise bottles, sealed and examined for the preservability at 30° C. Potato and carrot were boiled and cut into appropriate size before use. The period until emission of a putrid smell is defined as effective storage life. General living bacterial number of samples at that time was also measured. Results are shown in the following Table:

| | | Concentration (ppm) | pH | Storage life (hr) | Living bacteria (/g) |
|---|---|---|---|---|---|
| Group | 1 | 0.05 | 5.14 | 24 | $5.9 \times 10^6$ |
| | 2 | 0.5 | 5.15 | 30 | $2.8 \times 10^7$ |
| | 3 | 5.0 | 5.15 | 43 | $8.1 \times 10^6$ |
| | 4 | 50 | 5.16 | 56 | $5.5 \times 10^7$ |
| No addition | | 0 | 5.15 | 15 | $6.2 \times 10^6$ |

TEST EXAMPLE 7

Acute toxicity

Groups of two rats (Slc-ddY, male, 5 weeks old) were used as test animals.

The test animals orally received 1,000, 500, 250, 125 or 62.5 mg/kg of the test substance suspended in an aqueous solution of 5% gum arabic or subcutaneously injected with 500, 250, 125 or 62.5 mg/kg of the test substance suspended in sterilized injectable distilled water. One week after administration, general conditions and weight of the animals were examined. On the final day, the animals were sacrificed and their organs including lymph nodes were observed. At the dosage in the range of 1000 to 62.5 mg/kg (oral) and 500 to 6.25 mg/kg (s.c.). the test animals did not die and no visible disorder was observed in general physical conditions and organs at the sacrifice.

TEST EXAMPLE 8

Minimum growth inhibiting concentration:

The minimum growth inhibitory concentrations (MIC) of the bacterial substance UFC-N11 against various bacteria were according to conventional procedure the results are as follows:

| Pathogenic bacteria of fish disease | MIC (ug/ml) |
|---|---|
| Aeromonas hydrophila IAM108 (Aeromonas disease of carp) | 5.0 |
| Aeromonas salmonicida, MC7503 (Furunculosis of salmonids) | 1.25 |
| Vibrio anguillarum 25-1 (Vibrio disease of sweetfish) | 2.5 |
| Edwardssiella tarda 4-1 (Edwardsiellosis of eel) | 2.5 |
| Flexibacter columnaris V-II (Columnaris disease of eel) | 0.63 |
| Vibrio anguillarum K-3 (Vibrio disease of young yellowtail) | 2.5 |
| Pasteurella piscicida KGP86041 (Pseudotuberculosis of young yellowtail) | 0.16 |

TEST EXAMPLE 9

In vitro anti-bacterial activity

In accordance with the Chemical Therapeutics Academy standards, the anti-bacterial activity of UFC-N11 against the Pseudotuberculosis causative bacteria, Pasteurella piscicida, was examined. Among these pathogenic bacteria of Pseudotuberculosis collected in the field, there are many strains having acquired resistances against the commercially available anti-bacterial agents. Therefore, the anti-bacterial activity of UFC-N11 was measured using commercially available anti-bacterial agents as references. The results are shown in the following Table.

As seen in the Table, UFC-N11 shows excellent anti-bacterial activity on the strains which have shown the reduced sensitivity to the commercially available anti-bacterial agents.

| Antibacterial activity of UFC-N11 against Pseudotuberculosis causative bacteria, *Pasteurella pliscicida*: | | | | | | | | | | |
|---|---|---|---|---|---|---|---|---|---|---|
| | MIC (µg/ml) Strai | | | | | | | | | |
| Anti-bacterial agent | MS86115 | MS86169 | AT-1 | AT-17 | SP6275 | SP6291 | WP96 | MEP35 | MEP151 | KGP86041 |
| Nn-11 | 0.31 | 0.31 | 0.31 | 0.16 | 0.16 | 0.31 | 0.16 | 0.31 | 0.16 | 0.16 |
| Ampicillin | 0.039 | >10 | >10 | >10 | 0.039 | >10 | 0.078 | 0.039 | >10 | 0.039 |
| Oxolinic acid | 1.25 | 0.078 | 1.25 | 1.25 | 1.25 | 0.039 | 0.039 | 1.25 | 1.25 | 0.078 |
| Nifurstyrenic acid | 0.31 | 2.5 | 1.25 | 0.31 | 0.63 | 0.16 | 0.31 | 2.5 | 0.31 | 2.5 |

TEST EXAMPLE 10

Absorbance by oral administration

To a cultured yellowtail, UFC-N11 was compulsorily oral-administered at the rate of 100 mg/kg per body weight of fish. The tissue samples were collected 3, 8, and 24 hours later respective in order to determine the concentrations in the tissues. The results are shown in the following Table.

As shown in the Table, UFC-N11 was absorbed in concentrations which were equal to or in excess of the anti-bacterial activity.

Tests on absorption and secretion of UFC-N11 in yellowtail

| Time elapsed (hr) | Concentration in tissue (ug/ml, ug/g) | | | |
|---|---|---|---|---|
| | Plasma | Liver | Kidney | Muscle |
| 3 | 2.10 | 8.79 | 6.55 | 0.96 |
| 8 | 1.34 | 5.14 | 4.02 | 1.12 |
| 24 | <0.125 | 1.36 | 1.13 | <0.25 |

TEST EXAMPLE 11

Therapeutic effect of UFC-N11 in artificial infection of Pseudotuberculosis

The cultured young fishes of yellowtail (average body weight, 70–80 g) were subjected to bacterial bathing with Pasteurella piscicida DM-85 strain cultured at 25° C. for 24 hours in a bacterial suspension in artificial sea water ($10^3$ CFU/ml) for 5 minutes under aeration to make artificially infected fishes.

After the bathing with bacteria, 10 fishes each for allotment to each concentration section of UFC-N11 were put in a culture water tank, and from 1 hour after the bacterial bathing they were dosed with the prescribed amount of UFC-N11 by means of an oral probe at the rate of once a day for 5 days in total.

Judgement of the effect was carried out according to the mortality in 10 days after the artificial infection by bacterial bathing. The results are shown in the following Table.

As shown in the Table, UFC-N11 exhibits excellent therapeutic effect on noduloid disease of yellowtail.

Therapeutic effect of UFC-N11 in artificially infected Pseudotuberculosis

| Administration concentration (mg/kg of fish bodyweight) | Number of died fishes Number of days elapsed (day) | | | | | | | | | | | Mortality rate (%) |
|---|---|---|---|---|---|---|---|---|---|---|---|---|
| | 0 | 1 | 2 | 3 | 4 | 5 | 6 | 7 | 8 | 9 | 10 | |
| Control | 0 | 0 | 0 | 6 | 3 | 1 | | | | | | 100 |
| 100 | 0 | 0 | 0 | 0 | 0 | 0 | 0 | 0 | 0 | 0 | 0 | 0 |
| 50 | 0 | 0 | 0 | 0 | 0 | 0 | 0 | 0 | 0 | 0 | 0 | 0 |
| 20 | 0 | 0 | 0 | 3 | 1 | 0 | 0 | 0 | 0 | 0 | 0 | 40 |
| 10 | 0 | 0 | 0 | 4 | 3 | 1 | 0 | 0 | 0 | 0 | 0 | 80 |

What is claimed is:

1. A bacterial substance of the formula

2. A pharmaceutical composition comprising bactericidally effective amount of the bacterial substance UFC-N11 of the formula:

in association with a pharmaceutically acceptable carrier, dilute or excipient.

* * * * *